United States Patent [19]
Rosenfeld et al.

[11] Patent Number: 4,564,022
[45] Date of Patent: Jan. 14, 1986

[54] METHOD AND APPARATUS FOR INTRACRANIAL PRESSURE ESTIMATION

[76] Inventors: John G. Rosenfeld, 518A Sooner, Norman, Okla. 73069; Clark Watts, Rte. 4, Box 61; Donald H. York, 3714 Berrywood, both of Columbia, Mo. 65201

[21] Appl. No.: 357,482

[22] Filed: Mar. 12, 1982

[51] Int. Cl.$^4$ ............................................. A61B 5/00
[52] U.S. Cl. .................................. 128/748; 128/731
[58] Field of Search ......................... 128/748, 731–732

[56] References Cited

PUBLICATIONS

Guillet et al., "Digital Latencymeter"; *Med. and Biol. Eng. and Comput.*, Mar. 1977, vol. 15, No. 2, pp. 202–204.
Hartwell et al., "Evoked Potential Analysis: On Line Signal Optimization Using a Mini-Computer"; *EEG and Clin. Neurophys.*, vol. 41, No. 4, 10–1976, pp. 416–421.
York et al, "Relationship Between Visual Evoked Potentials and Intracranial Pressure", *J. Neurosug.*, vol. 55, pp. 909–916, (12/81).
Sutton et al, "The Effects of Cold-Induced Brain Edema and White-Matter Ischemia on the Somatosensory Evoked Response", *J. Neurogurg.*, pp. 180–184.
York et al, "Estimation of Intracranial Pressure by Measurement of Visual Evoked Potentials", IEEE/Engineering in Med. & Bio. Conf. Oct. 6–7, 1979.
Gaab et al, "EEG, Cerebral Metabolic Disorder and Intracranial Pressure in Experimental Bain Edema Before and After Therapy" *Acta. Neurol. Scand.* pp. 518–519.
Branston et al, "Relationship Between the Cortical Evoked Potential and Local Cortical Blood Flow Following Acute Middle Creebral Artery Occulsion in the (cont. of above) *Experimental Neurol.*, vol. 45, pp. 195–208 (1974).
Jeffreys et al, "Source Locations of Pattern-Specific Components of Human Visual Evoked Potentials I. Component of Striate Cortical Origin", *Exp. Brain Res.*, vol. 16, pp. 1–21 (1972).
Cohn, "Visual Evoked Responses in the Brain Injured Monkey", *Arch. Neurol.*, vol. 21, pp. 321–329 (1969).
Ellingson, "The Study of Brain Electrical Activity in Infants", *Adv. Child. Dev. Behav.*, vol. 3, pp. 53–97 (1967).
Ellingson, "Cortical Electrical Responses to Visual Stimulation in the Human Infant", *Electroencphalogr. Clin. Neurol.*, vol. 12, pp. 663–677 (1960).
Allen, A. R., Starr, A., "Sensor Evoked Brain Potentials in the Operating Room", Neurology 27:358, 1977.
Branston, N. M., Symon, L., Crockard, H. A., "Recovery of the Cortical Evoked Response Following Temporal Meddle Cerebral Artery Occlusion in Baboons: Related to Local Blood Flow and PO$_2$", Stroke 7:151–157, 1976.
Brock, M., Beck, J., Markakis, E., et al., "Intracranial Pressure Gradients, Local Tissue Perfusion Pressure and Regional Cerebral Blood Flow", Eur Neurol 8:74–78, 1972.
Carlow, T. J., "Visual Evoked Response (VER) in Neuro-Ophthalmology, in Smith, J. L. (ed), Neuro-Ophthalmology Focus, 1980, New York Masson, 1979, pp. 237–246.

(List continued on next page.)

*Primary Examiner*—Lee S. Cohen
*Assistant Examiner*—Angela D. Sykes
*Attorney, Agent, or Firm*—Richards, Harris, Medlock & Andrews

[57] ABSTRACT

A method and apparatus for non-invasively estimating the intracranial pressures of a subject is provided. A sensory stimulus is directed towards the subject thereby generating electrical brain activity. A peak in the second negative-going wave of the brain activity is identified and the latency of such peak is measured. The intracranial pressure of the subject is estimated by comparing value of the latency with known latency/intracranial pressure correlations.

23 Claims, 10 Drawing Figures

OTHER PUBLICATIONS

Clague, B., Lorig, R. J., Weiss, M. H. et al, "Comparative Effects of Increased Intracranial Pressure Upon Cerebral Oxygenation, Cortical Evoked Potential and Brain Survival", Stroke, 4:346, 1973.

Crockard, H. A., Brown, F. D., Trimble, Jr., et al, "Somatosenorsy Evoked Potentials, Cerebral Blood Flow and Metabolism Following Cerebral Missile Trauma in Monkeys", Surg Neurol 7:281-287, 1977.

Dustman, R. E., Schenkenberg, T., Lewis, E. G., et al, "The Cerebral Evoked Potential: Life-Span Changes and Twin Studies, in Desmedt, J. E. (ed): Visual Evoked Potentials in Man: New Developments, Oxford: Clarendon Press, 1977, pp. 363-380.

Ellingson, R. J., "The Study of Brain Electrical Activity in Infants", Adv. Child Dev. Behav. 3:53-94, 1967.

Engel, R. C., "Abnormal Electroencephalograms in the Neonatal Period", Springfield, Ill, Charles C. Thomas, 1975, pp. 106-116.

Feinsod, M. Selhorst, J. B., Hoyt, W. F., et al, "Monitoring Optic Nerve Function During Craniotomy, J. Neurosurg 44:29-31, 1976.

Gaab, M., Knoblich, O. E., Dietrich, K., et al, "Therapy of Experimental Brain Edema in Cats, in Wullenweber, R., Brock, M., Hamer, J., et al. (eds), Lumbar Disc. Adult Hydrocephalus, Advances in Neurosurgery, vol. 4, Berlin, Springer-Verlag, 1977, pp. 214-224.

Greenberg, P. R., Becker, D. P., Miller, J. D., et al, "Evaluation of Brain Function in severe Human Head Trauma with Multimodality Evoked Potentials:, Part 2, Localization of Brain Dysfunction and Correlation with Posttraumatic Neurological Conditions".

Greenberg, R. P., Mayer, D. J., Becker, D. P., "Correlation in Man of Intracranial Pressure and Neuroelectric Activity Determined by Multimodality Evoked Potentials, in Beks JWF, Bosch, D. A., Brock, M. (eds), Intracranial Pressure III, Berlin/Heidelberg.

Grossman, R. G., Turner, J. W., Miller, J. D., et al. "The Relationship Between Cortical Electrical Activity, Cerebral Perfusion Pressure and Cerebral Blood Flow During Increased Intracranial Pressure", in Langfitt, T. W., McHenry, L. C., Jr., Reivich, M.

Halliday, A. M., McDonald, W. I., Mushin, J., "Visual Evoked Response in Diagnosis of Multiple Sclerosis, Br. Med. J., 4, 661-664, 1973 Harter, M. R., White, C. J., "Effect of Contour Sharpness and Check-size on Visually Evoked Cortical Potentials", Vision Res. 8:701-711, 1968.

Hume, A. L., Cant, B. R., Shaw, N. A., "Central Somatosensory Conduction Time in Comatose Patients", Ann Neurol 5:379-384, 1979.

Jeffreys, D. A., Axford, J. G., "Source Locations of Pattern-Specific Components of Human Visual Evoked Potentials" II. Component of Extrastriate Cortical Origin, Exp Brain Res 16:22-40, 1972.

Milner, B. A., Regan, D., Heron, J. R., "Differential Diagnosis of Multiple Sclerosis by Visual Evoked Potential Recording", Brain 97:755-772, 1974.

Ommaya A. K., Gennarelli, T. A., "Cerebral Concussion and Traumatic Unconsciousness" Correlation of Experimental and Clinical Observations of Blunt Head Injuries", Brain 97:663-654, 1974.

Oosterhuis, H. J., Ponsen, L., Jonkman, E. J., et al, "The Average Visual Response in Patients with Cerebrovascular Disease", Electroencephalogr Clin Neurophysiol 27:23-34, 1969.

Robinson, F., "Influence of Increased Intracranial Pressure on Evoked Responses to Sensory Stimulation", Electroencephalogr Clin Neurophysiol 23:96, 1967.

Sklar, F. H., Ehle, A. L., Clark, W. K., "Visual Evoked Potentials: A Noninvasive Technique to Monitor Patients with Shunted Hydrocephalus, Neurosurgery 4:529-534, 1979.

Sokol, S., "Visually Evoked Potentials: Theory, Techniques and Clinical Applications", Surv Ophthalmol 21:18-44, 1976.

Starr, A., "Sensory Evoked Potentials in Clinical Disorders of the Nervous System", Ann Rev Neurosci 1:103-127, 1978.

Sutton, L. N., Bruce, D. A., Welsh, F., "The Effects of Cold-Induced Brain Edema and White-Matter Ischemia on the Somatosensory Evoked Response", J Neurosurg 53:180-184, 1980.

Wright, J. E., Arden, G., Jones, B. R., "Continuous Monitoring of the Visually Evoked Response During Intra-Orbital Surgery, Trans Ophthalmol Soc UK 93:311-314, 1973.

METHOD AND APPARATUS FOR INTRACRANIAL PRESSURE ESTIMATION

TECHNICAL FIELD

The present invention relates to the estimation of intracranial pressure, and more particularly to a method and apparatus for the non-invasive estimation of intracranial pressure.

BACKGROUND ART

It is often desirable to assess the intracranial pressure of a patient. For example, in the course of treatment of hydrocephalus the estimation of intracranial pressure is a useful tool for the assessment of shunt malfunction. By way of further example, patients with cerebral edema secondary to head trauma often suffer from increased intracranial pressure, and it is necessary to measure or estimate such pressure in order to diagnose and treat the increased intracranial pressure.

At present, intracranial pressure can be measured only by invasive techniques. For example, one common technique for measuring intracranial pressure involves the insertion of a pressure transducer directly into the epidural space through a burr hole. The pressure may then be displayed and recorded using conventional techniques. In shunted hydrocephalic patients, intracranial pressure may be measured manometrically by direct puncture of the shunt. Invasive methods of intracranial measurements suffer from numerous drawbacks, including the trauma involved in placing measurement devices, as well as the time involved in using such equipment.

Visual evoked potentials are electrical brain signals which are caused by visual stimulation, such as the observance of a flashing light. The characteristics of visual evoked potentials are relatively well-defined in both the maturing child and the adult. Visual evoked potentials have been used to provide information about a variety of characteristics, such as visual acuity, diseases of the optic nerve and chiasm, color blindness, and other problems of vision. Visual evoked potentials are also used to monitor surgery around the optic nerves and chiasms and to assess effects of hypotension and brain retraction. Evidence of edema, contusion or other traumas within the temporal, parietal, and occipital lobes has been demonstrated by using visual evoked potentials. Visual evoked potential measuring has also been used to determine a variety of other brain-related characteristics, such as intelligence, brain memory, sensory perception, and local dysfunction.

DISCLOSURE OF THE INVENTION

The present invention provides a method and apparatus for estimating intracranial pressure by the measurement of visual evoked potentials. It is now known that there is direct correlation between the latency of the second negative-going wave ("N2 wave") of a visual evoked potential and intracranial pressure. An accurate estimate of a subject's intracranial pressure can thus be made by measuring the latency of the N2 wave. Apparatus is provided to automate the production of visual evoked potentials, to isolate the peak of the N2 wave, to correlate the N2 latency with intracranial pressure and to display the estimated intracranial pressure range.

The method and apparatus of the present invention provides a non-invasive measure of intracranial pressure. Accordingly, the present invention has numerous advantages over prior art invasive methods of measuring intracranial pressure. The preferred form of the invention, which utilizes microprocessor technology, lends itself to compact manufacture and simple operation. This should be contrasted with prior art methods of measuring visual evoked potentials, which all involved complex and expensive apparatus. Other aspects and advantages will become apparent hereinafter.

BRIEF DESCRIPTION OF THE DRAWINGS

A more complete understanding of the invention and its advantages will be apparent from the Detailed Description taken in conjunction with the accompanying Drawings in which.

DETAILED DESCRIPTION

Figure 1:
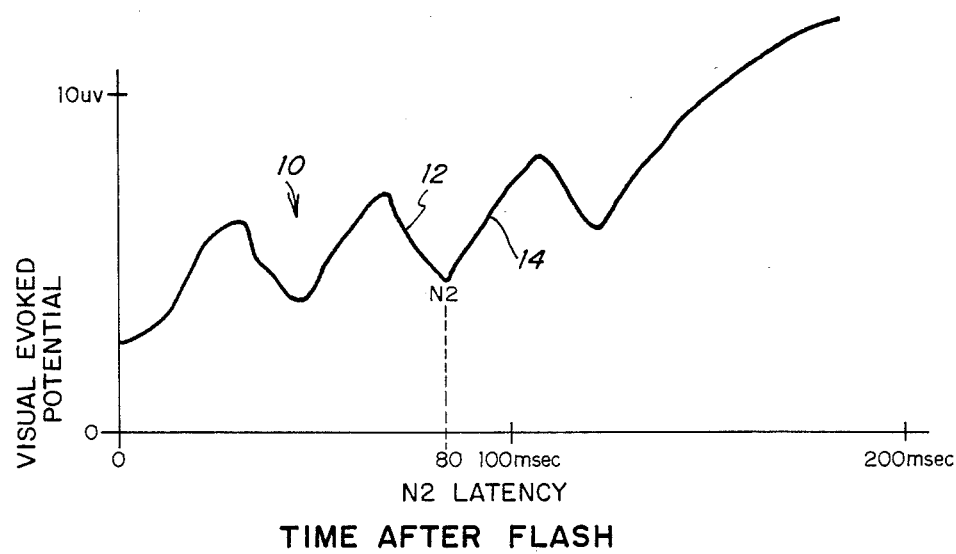
FIG. 1 is a graph illustrating a visual evoked potential and the latency of the N2 wave.

Referring initially to FIG. 1, an electroencephalogram signal induced by a light flash is shown plotted with respect to time after the flash. This signal is referred to as a "visual evoked potential". The vertical axis of the graph represents a differential microvolt signal detected by standard EEG equipment, and the horizontal axis represents the time after a flash measured in milliseconds. Waveform 10 includes second negative-going wave section 12, which terminates at a peak designated by the reference figure "N2". At point N2, waveform 10 undergoes a change in slope from negative to positive, continuing as third positive-going wave section 14. As illustrated by the dashed line below N2, waveform 10 has an N2 latency of approximately 80 milliseconds. It will be understood that potentials such as waveform 10 can be evoked by a variety of different sensory stimuli, and this specification and the claims which follow are expressly intended to include auditory stimulus as well as other equivalents of visual stimulus to evoke electrical brain wave activity.

N2 latency is now known to be directly related to intracranial pressure. The correlation between N2 latency and intracranial pressure ("ICP") is as set forth in the following table:

| ICP (mmH$_2$O) | N2 Latency (msec) |
| --- | --- |
| 50–100 (normal) | 60–68 |
| 100–200 (normal) | 68–76 |
| 200–300 (slight elevation) | 76–84 |
| 300–400 (significant elevation) | 84–92 |
| 400–500 (significant elevation) | 92–100 |
| 500–700 (high elevation) | 100–108 |

As illustrated by the table, an increase of intracranial pressure will be accompanied by a corresponding increase in N2 latency. The time range in which the N2 peak may be expected is within the interval of approximately 60 to 108 milliseconds after flash. According to the known characteristics of visual evoked potentials, only one negative-going peak, or change in slope from negative to positive, will occur within this range, and therefore, measuring the latency of a negative to positive slope change within the range of 60 to 108 milliseconds should always identify the N2 peak.

Figure 2:
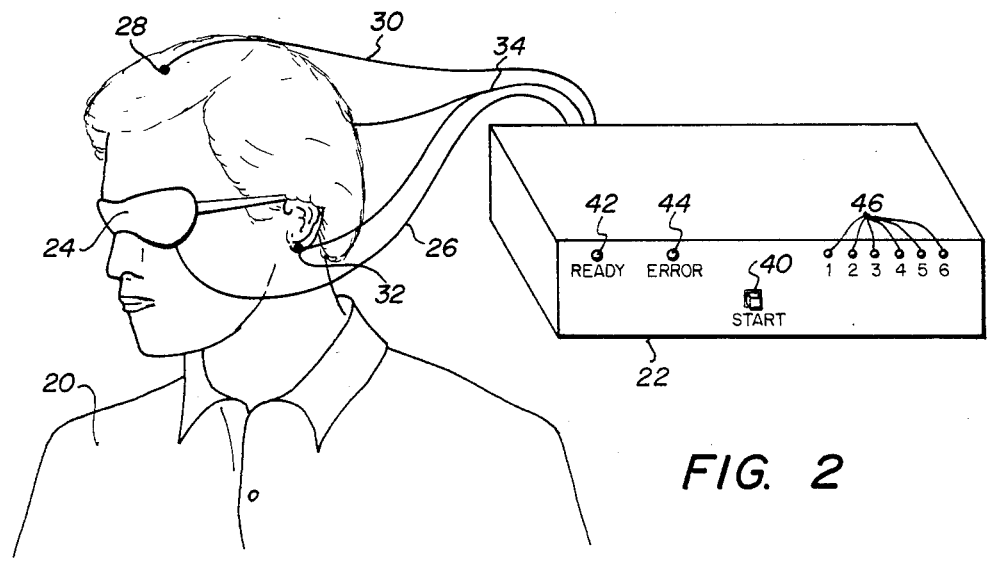
FIG. 2 is a perspective view of apparatus constructed in accordance with the invention.

Referring now to FIG. 2, subject 20 is shown connected to apparatus for carrying out the method of intracranial pressure estimation of the present invention. Apparatus constructed in accordance with invention includes monitor 22 and goggles 24. Goggles 24 are fitted with neon lamps to stimulate both eyes simultaneously. It will be understood that a strobe-flash may also be used to stimulate the eyes. Goggles 24 are connected to monitor 22 by means of cable 26. Standard EEG electrode 28 is affixed to the scalp of subject 20 at the vertex (Cz) according to the International 10-20 System. Electrode 28 is connected to monitor 22 by means of cable 30. Reference electrode 32 is connected to the left earlobe of subject 20 and a second reference electrode (not shown) is connected to the right earlobe. The two reference electrodes are linked together and are connected to monitor 22 by means of cable 34. A ground electrode (not shown) is placed on a forearm of subject 20. Under standard conditions, the electrode impedance will be under 5,000 ohms.

Monitor 22 includes start switch 40, "ready" light 42, "error" light 44 and six intracranial pressure range indicators 46.

Figure 3:
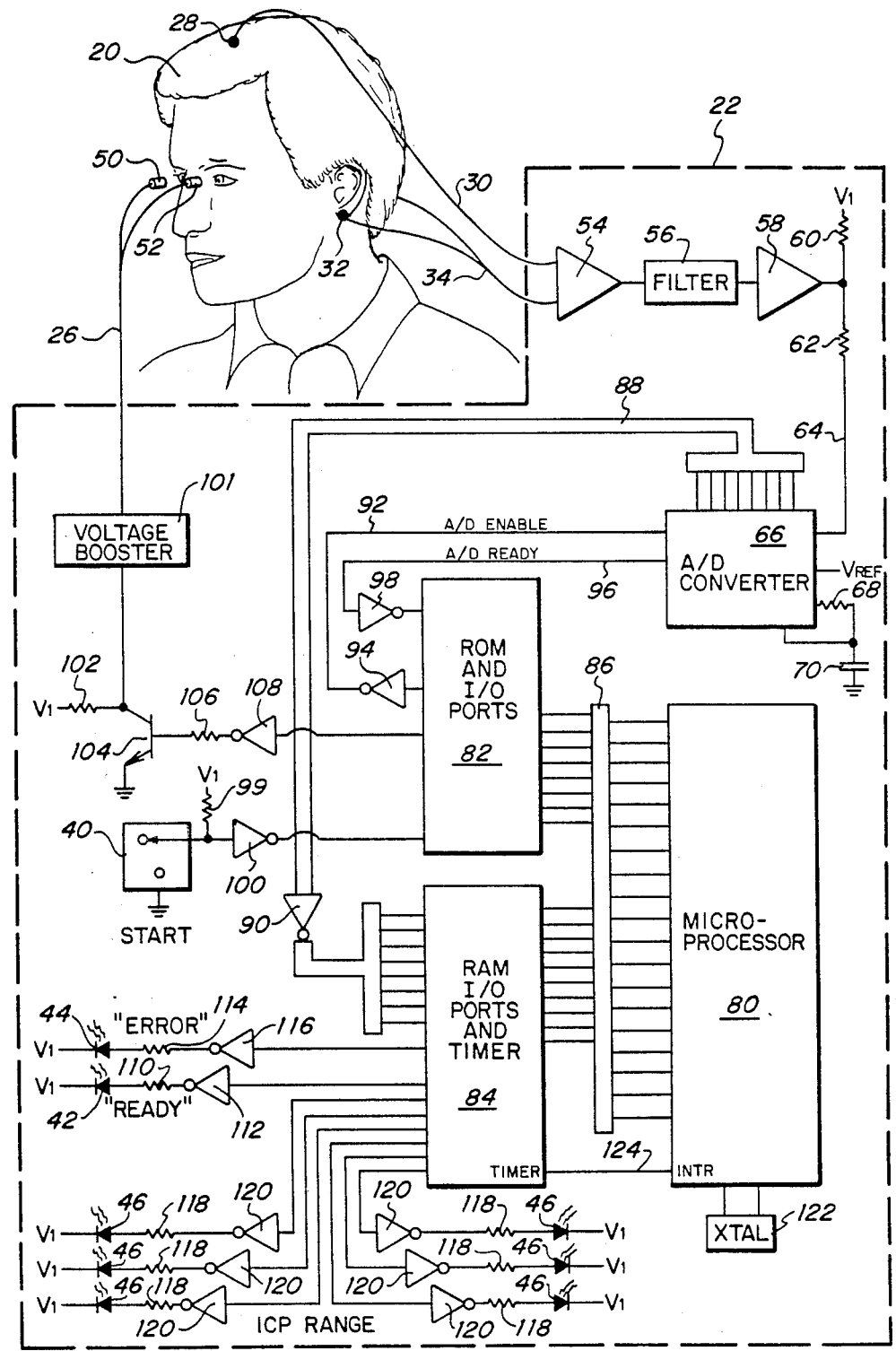
FIG. 3 is a circuit schematic of the device shown in FIG. 2.

Referring now to FIG. 3, goggles 24 (not shown) include neon lamps 50 and 52. Cables 30 and 34 are connected to differential amplifier 54. The differential signal output of amplifier 54 passes through bandpass filter 56 to amplifier 58. Filter 56 has a bandpass of 1-30 Hz and amplifier 58 has a gain of 100,000. Amplifiers 54 and 58 and filter 56 are standard apparatus used in electroencephalography and will not be described further. Any high-gain, low-noise general purpose physiological differential amplifier which includes bandpass filtering may be used.

The output of amplifier 58 is connected to a voltage divider composed of resistors 60 and 62. One end of resistor 60 is connected to main supply voltage $V_1$, which in preferred form is approximately 5 volts. An end of resistor 62 is connected by line 64 to the input pin of analog-to-digital converter 66.

Analog-to-digital converter 66 in preferred form is an 8-bit converter manufactured by National Semi-Conductor and designated by model number ADC804. A reference voltage of 2.5 volts, $V_{ref}$, is attached to the ADC804 as recommended by the manufacturer. A clock circuit composed of resistor 68 and capacitor 70 slows the internal clock of analog-to-digital converter 66. The clock circuit is necessary because of the slow speed of the microprocessor system clock.

Control of monitor 22 is provided by a microprocessor-based system composed of microprocessor 80 and support chips 82 and 84. In preferred form, microprocessor 80 is a 8085A microprocessor manufactured by Intel Corporation. Support chip 82 is an Intel 8355 ROM and input/output ports device and support chip 84 is an Intel 8155 RAM, input/output ports and timer device. Microprocessor 80 and support chips 82 and 84 are interconnected by control, address and data busses 86 in accordance with standard techniques. Reference is made to the *MCS-80/85* ™ *Family User's Manual*, dated October, 1979 and published by Intel Corporation, for basic information relating the 8085A microprocessor system. It will be understood that the apparatus of the present invention is not limited to a microprocessor system, but may be used with any general purpose digital computer.

The 8-bit output of analog-to-digital converter 66 enters an input port of support chip 84 via bus 88 and buffers 90. Line 92 carries an "enable" signal from support chip 82 through buffer 94 to analog-to-digital converter 66. Analog-to-digital converter 66 returns a "ready" signal to support chip 82 via line 96 and buffer 98.

"Start" switch 40 is a SPST switch having a pole normally held at $V_1$ through resistor 99. When activated, switch 40 switches the pole to ground, causing inverter 100 to input a high logic signal to an input port of support chip 82.

Line 26 connects neon lamps 50 and 52 to voltage booster 101. Voltage booster 101 is connected to the junction of resistor 102 and the collector of transistor 104. Resistor 102 is connected at its other end to $V_1$. Voltage booster 101 may be any neon lamp driver known in the art, such as a silicon-controlled rectifier or relay. The emitter of transistor 104 is connected to ground, and the base of transistor 104 is connected through resistor 106 to inverter 108. The input of inverter 108 is connected to an output port of support chip 82.

"Ready" light 42 is a light-emitting diode connected to $V_1$ and to an output port of support chip 84 through resistor 110 and inverter 112. In similar fashion, "error" light 44 is connected to $V_1$ and to an output port of support chip 84 through resistor 114 and inverter 116. Intracranial pressure range indicators 46 are light-emitting diodes, and each is connected to a separate output port of support chip 84 through a resistor 118 and inverter 120. Each diode 46 is also connected to an $V_1$.

Crystal 122 is connected to microprocessor 80 in standard fashion to set the frequency of the system clock. The timer output of support chip 84 is connected to an interrupt pin of microprocessor 80 through line 124.

In operation, the estimation of intracranial pressure involves a fitting electrodes 28 and 32 to subject 20 and fitting subject 20 with goggles 24. Monitor 22 is then energized, and "ready" light 42 is illuminated when monitor 22 is ready to take data. Depressing "start" switch 40 causes microprocessor 80 to execute software, described in more detail below, which causes neon lamps 50 and 52 to flash, thereby generating visual evoked potentials in electrodes 28 and 32. Monitor 22 converts the amplified analog output in line 64 to a plurality of discrete digital values by means of analog-to-digital converter 66. In preferred form, analog-to-digital converter 66 is enabled to read a discrete data point every 0.5 milliseconds starting 60 milliseconds after a flash and ending 108 milliseconds after flash. A total of 96 discrete points of digital data are taken following each flash. A running sum of the values of each discrete digital point is stored in a separate memory address in the RAM of support chip 84. In preferred form, a total of 32 flashes are sent at one second intervals. Each memory address contains a running sum of the digital values of each point along the visual evoked potentials.

After all the visual evoked potentials have been stored in discrete digital form, microprocessor 80 causes the sum total for each discrete point to be averaged by dividing by 32. This results in a 96-point average visual evoked potential for the interval of 60 to 108 milliseconds. As described above, any negative to positive slope change within this interval should represent the N2 peak. Microprocessor 80 determines such a slope change and identifies its location in memory, thereby determining the N2 latency value. Lastly, an intracranial pressure range light 46 is illuminated to generate an output signal representative of the N2 peak location and to indicate estimated intracranial pressure.

Figure 4:
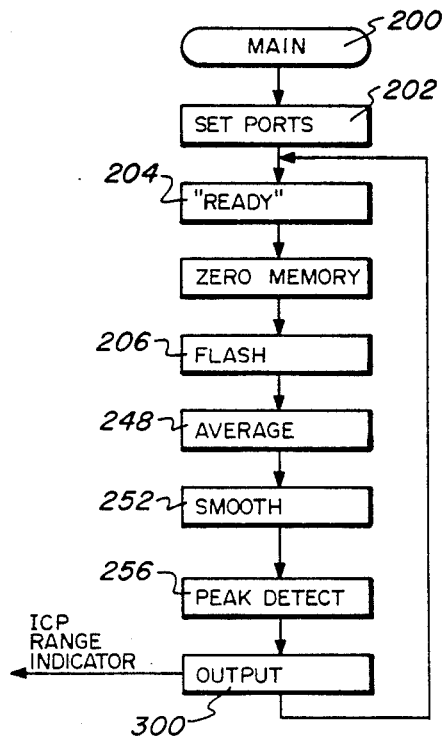
FIGS. 4 THRU 10 are flow charts of software particularly adapted to carry out the method of the present invention.
Figure 5:
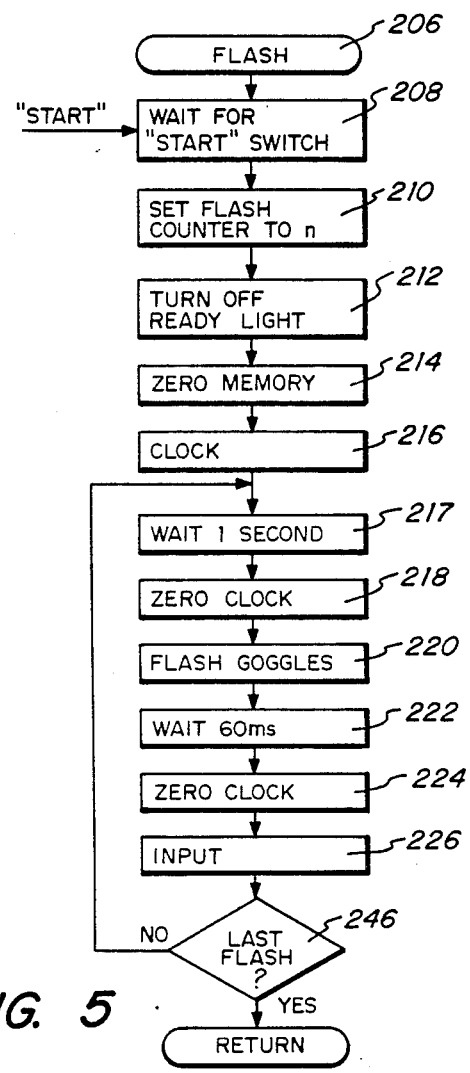

Referring now to FIG. 4, the monitor software is divided into control logic which runs the monitor and computational logic which calculates the intracranial pressure estimate. In preferred form, the software is in the form of machine code stored in the ROM section of support chip 82. FIG. 4 illustrates program "main" 200, which has two functions. The first function is accomplished by step 202 which initializes the hardware shown in FIGS. 2 and 3 of monitor 22. The initialization function includes setting the various input/output ports of support chips 82 and 84 in step 202. This function is accomplished when the monitor is initially turned on. A "reset" switch may be provided to facilitate this function. The second function of program "main" 200 is calling the various subroutines described below, which provide logic for controlling monitor 22. Once step 202 is finished, step 204 causes "ready" light 42 to be illuminated. Program "main" 200 then calls "flash" subroutine 206, which is illustrated in more detail in FIG. 5.

"Flash" subroutine 206 includes the logic which causes monitor 22 to flash goggles 24 and take data points along the resulting visual evoked potentials. These functions are accomplished by means of several nested subroutines within "flash" subroutine 206. Step 208 of subroutine 206 causes monitor 22 to go into a WAIT loop, during which an input port of support chip 82 is monitored for a transition in logic caused by the user depressing "start" switch 40. Subroutine 206 senses this transition and jumps out of the loop to execute step 210, which sets the flash counter to a pre-determined "n" number of flashes (in preferred form, 32). Step 212 is then executed, which turns off "ready" light 42. Step 214 places zeros in the section of support chip 84 RAM which will hold the 96-point digital representation of the visual evoked potentials. Step 216 sets up the primary timing logic, which is interrupt driven by support chip 84. The timing logic enables the 60 millisecond interval described and the one second interval of step 217. Step 218 resets the clock to zero in preparation for a flash/input cycle. Step 220 then causes the goggles to flash by causing the input of inverter 108 to shift to a high logic state. This causes transistor 104 to cease conducting, thereby lighting neon lamps 50 and 52 through voltage booster 101. The monitor is then caused to wait 60 milliseconds after the flash by step 222. This 60 millisecond delay is necessary to reach the significant time interval in the evoked potential where the N2 peak will be present. After 60 milliseconds have elapsed, the clock is reset to zero in step 224 and "input" subroutine 226 is called.

Figure 6:
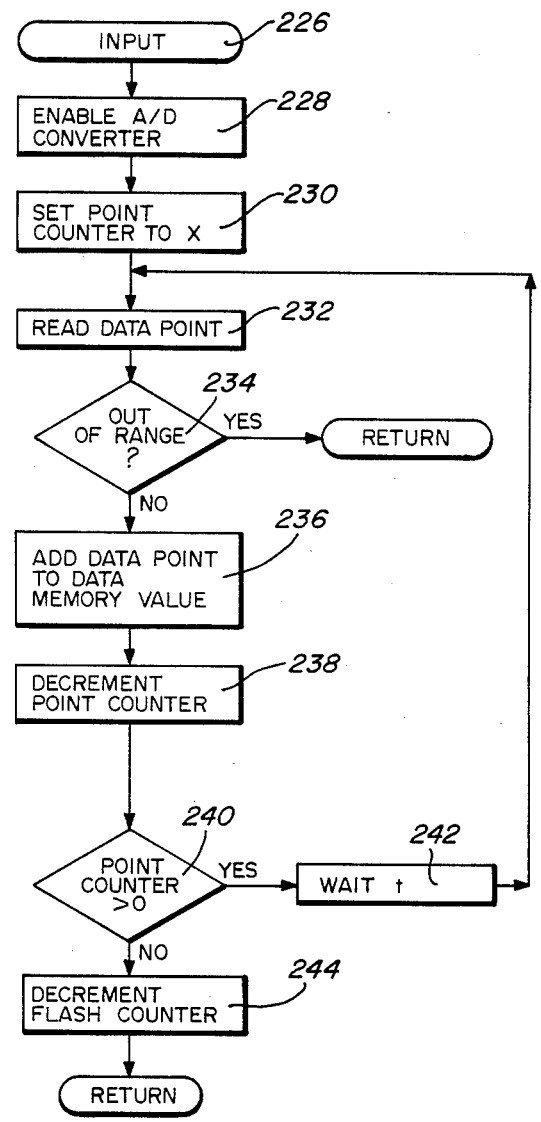

"Input" subroutine 226 is illustrated in FIG. 6. Step 228 causes analog-to-digital converter 66 to be enabled by means of a signal from an output port of support chip 82 through inverter 94 and line 92. Step 230 sets the point counter to "x", which in preferred form equals 96. The first data point is read in step 232 and is tested for an out-of-range condition in step 234. If the data point is out-of-range, control is returned to "flash" subroutine 206 at step 246 to cause another flash without decrementing the flash counter. If the data point is within the proper range, the data point is added to the data memory value corresponding to the first data point in step 236. The point counter is then decremented in step 238. If the point counter is greater than zero, as determined in step 240, a time period "t" is waited in step 242, which in preferred form equals 0.5 milliseconds. The logic then returns to step 232 to read another data point. After all of the data points have been taken and recorded in their respective data memory locations, the flash counter is decremented in step 244. Control is then returned to "flash" subroutine 206 at step 246. At step 246, the flash counter is tested to determine if the all the flashes have been delivered. If not, the logic returns to step 217 to wait one second before initiating another flash/input cycle. If all of the flashes have been delivered, control is returned to program "main" 200.

Figure 7:
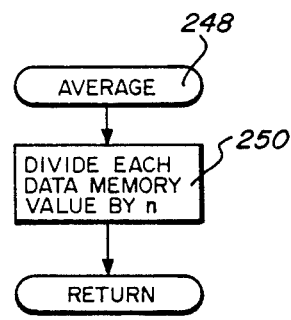

Subroutine "average" 248, illustrated in FIG. 7, is called by program "main" 200 to obtain the average visual potential of the n visual evoked responses. This average potential is derived in order to improve the signal-to-noise ratio. The evoked potentials have been summed already in the n flash/input cycles. "Average" subroutine divides each of the x data memory values by n to get an average evoked potential. In the preferred embodiment, where n equals 32, division is accomplished by rotation of each memory location from the most significant bit to the least significant bit five times. Each rotation causes the data memory value to be divided by 2, and so division by 32 is accomplished by rotating five times. This is performed on all 96 memory locations in step 250, and then control of the logic is returned to "main" program 200.

Figure 8:
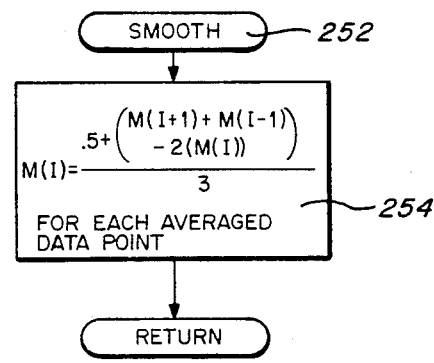

Subroutine "smooth" 252 illustrated in FIG. 8 eliminates random voltage fluctuations and extraneous electrical noise from the average evoked potential. Elimination is accomplished by "curve smoothing" using a standard three-point curve smooth equation:

$$m(I) = .5 + \frac{m(I + 1) + m(I - 1) - 2(m(I))}{3}$$

where m(I) equals the data memory value at location I. This equation is performed in step 254 for each averaged data point and then control is returned to program "main" 200.

The next step in the logic involves the location of the N2 peak, which is represented by a change in slope from negative to positive within the data set time range. This function is accomplished in "peak detect" subroutine 256 illustrated in FIG. 9.

"Peak detect" subroutine 256 is designed to find the N2 peak, calculate the latency of the N2 peak and reject the data if more than one negative-going peak is found or if no negative-going peak is found. The "peak detect" subroutine 256 relies on correct timing of the previous programs to provide an interval where only the N2 peak resides.

The method of "peak detection" utilized in this subroutine involves locating a change in slope from negative to positive along the visual evoked potential. Since only the N2 peak is in the time domain stored by the previous subroutines, a change in slope should occur only once. To guard against small artifactual voltage fluctuations in the wave form, a large change in slope with time is looked for first. This is accomplished by looking for a negative difference between the magnitude of one data memory value of the visual evoked potential and a second data memory value 4 milliseconds away. Once the peak has been isolated within a 4 millisecond interval, the precise location of the peak is determined by examining the 4 millisecond interval in 0.5 millisecond steps. The logic allows one and only one negative peak, or else the data will be rejected and "error" light 44 will be illuminated.

Figure 9:
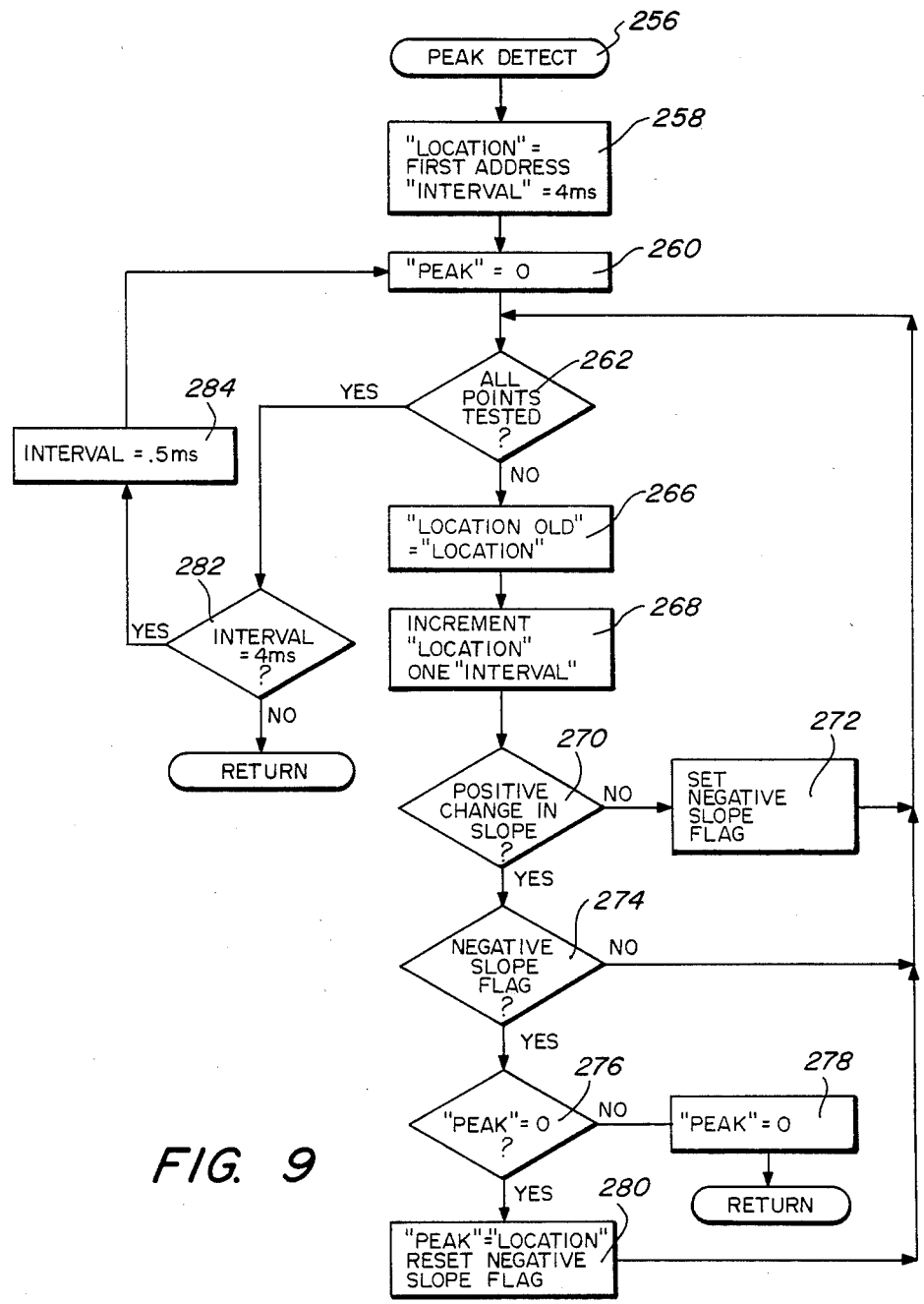

Referring now to FIG. 9, the "peak detect" subroutine is illustrated in detail.

The subroutine is initialized in step 258, where register "location" is set to the first memory location of the visual evoked potential and register "interval" is set to four milliseconds. In step 260 memory location "peak" is set to zero. In step 262, it is determined whether all x points have been tested; if so, the logic branches to step 264. In step 266, register "location old" is set to the value of register "location", and in step 268 register "location" is incremented by the value stored in "interval". The two data memory values designated by the addresses in registers "location" and "location old" are tested in step 270 to determine if the slope between the values is positive. If the slope is not positive, i.e., it is negative, the "negative slope" flag is set in step 272. The logic then branches back to step 262 to determine whether all x points have been tested. If a positive change in slope is found in step 270, step 274 determines whether the slope in the preceding pair of data values was negative by examining the "negative slope" flag. If not, the logic branches back to step 262 to determine whether all points have been tested. If the "negative slope" flag was set, in step 276 it is determined whether memory value "peak" equals zero. If "peak" does not equal zero, this means that at least one peak has already been identified and that more than one peaks in this data set have been found. In step 278, therefore, memory value "peak" is reset to zero and control is returned to program "main" 200. It will be recalled that a zero in memory value "peak" indicates that an error has been identified in the "peak detect" subroutine. If it is determined in step 276 that "peak" equals zero, then "peak" is set to the value of register "location" and the "negative slope" flag is reset in step 280. The logic then branches back to the step 262 to determine if all points have been tested.

When all the points have been tested, it is determined in step 282 whether register "interval" in the preceding steps was four milliseconds. When register "interval" equals four milliseconds, the preceding logic has just isolated a peak in a large interval. In step 284, register "interval" is set to 0.5 milliseconds to enable the precise location of the peak. The logic then returns to step 260 where memory value "peak" is reset to zero to enable a second iteration of the peak location logic. The second iteration begins with register "location" equalling the memory value "peak". Logic steps 262 through 280 are then executed again, with register "interval" being 0.5 milliseconds. When all points in the large interval have been tested, as determined in step 262, the logic returns to program "main" 200 as a result of the determination of step 282.

After the "peak detect" subroutine has executed, either a zero or a number ranging from 2 1 to 196 is stored in the memory location "peak" representing the peak location. It will be recalled that a zero in "peak" indicates that an error has been identified in the "peak detect" subroutine. As shown in FIG. 4, after subroutine "peak detect" has been executed, program "main" 200 advances to "output" subroutine 300.

Figure 10:
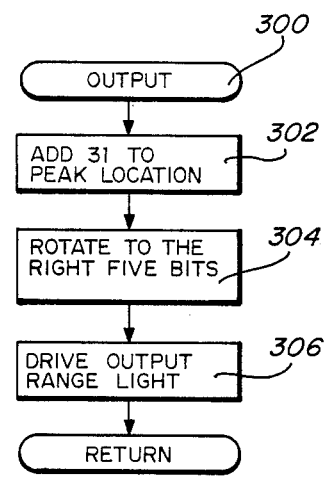

Referring now to FIG. 10, where "output" subroutine 300 is illustrated in detail, step 302 causes a 31 to be added to memory location "peak" representing the peak location. The addition of 31 in step 302 allows the subsequent logic to recognize an error. The peak location is then divided by 32 in step 304 using the method of five rotations described above in connection with step 250. Where "peak" was either a zero or a number between 2 and 196, this produces the numbers ranging from zero to 6, where zero stands for error, 1 for a normal range of intracranial pressure (latency 60–68 msec), 2 for the next normal range of intracranial pressure (latency 68–76 msec), 3 for slight elevation range of pressure (latency 76–84 msec), 4 for significant elevation range of pressure (latency 84–92 msec), 5 for the next significant elevation range of pressure (latency 92–100 msec), and 6 for highest range of pressure (latency 100–108 msec). The numbers 1 to 6 calculated in the "output" subroutine correspond to the table of latency/intracranial pressure correlations set forth above in the table. In step 306 the appropriate ICP range indicator 46 is illuminated to correspond with the numbers calculated in step 304. The program logic then returns to program "main" 200, which loops back to step 204, wherein the "ready" light 42 is illuminated to calculate another estimated intracranial pressure.

It can thus be seen that the present invention provides a method and apparatus to non-invasively estimate intracranial pressure. The combination of a general purpose micro-computer and specific software enables the production of a relatively inexpensive device to perform such intracranial pressure estimation.

While a particular embodiment of the present invention has been described in detail herein and shown in the accompanying drawings, it will be evident that various further modifications are possible without departing from the scope of the invention.

We claim:

1. A method for estimating intracranial pressure comprising the steps of:
   (a) generating at least one evoked potential;
   (b) measuring the value of the latency of a peak of said evoked potential; and
   (c) comparing the value of said latency with known latency/intracranial pressure correlations to determine an estimated intracranial pressure.

2. The method of claim 1 wherein a plurality of evoked potentials are generated and an average peak latency is determined.

3. The method of claim 1 wherein said peak is the second negative-going peak of said at least one evoked potential.

4. A method of estimating the intracranial pressure of a subject comprising the steps of:
   (a) attaching an electrode to the subject's head to measure potentials;
   (b) providing a sensory stimulus to the subject to produce an evoked potential;
   (c) measuring the interval between said sensory stimulus and a peak voltage potential on said electrode; and
   (d) identifying an estimated range of intracranial pressure corresponding to said measured interval.

5. The method of claim 4 wherein said interval is in the range of approximately 60 to 108 milliseconds.

6. The method of claim 4 wherein a first electrode is placed on the subject's skull vertex, a second electrode is placed on the subject's left earlobe, and a third electrode is placed on the subject's right earlobe, and said peak voltage potential is a differential voltage between said first electrode and said second and third electrodes.

7. The method of claim 4 wherein said peak voltage potential is the second negative-going peak of said voltage potential.

8. A method for estimating the intracranial pressure of a subject comprising the steps of:
(a) evoking a potential by means of a sensory stimulus;
(b) recording the values of a plurality of discrete points along said potential in the time range of approximately 60 to 108 milliseconds after said stimulus;
(c) analyzing said values to determine the location of a change in slope from negative to positive along said potential in said time range; and
(c) calculating a range of estimated intracranial pressure corresponding to said location of said change in slope.

9. The method of claim 8 further comprising the step of reiterating said step of evoking a potential a predetermined number of times.

10. The method of claim 9 further comprising the step of averaging said recorded discrete point values.

11. A method of estimating the intracranial pressure of a subject comprising the steps of:
(a) providing at least one sensory stimulus to the subject;
(b) sensing an analog electrical brain response of the subject to said at least one stimulus by means of an electrode;
(c) converting said analog response to a digital signal;
(d) determining a peak location in said digital signal by means for digital computing;
(e) generating an output signal representative of said peak location to indicate estimated intracranial pressure;
(f) wherein said analog response is sampled at a plurality of intervals such that a plurality of discrete digital values are generated which represent said analog response; and
(g) wherein said discrete digital values are generated within the time interval of approximately 60 to 108 milliseconds after each stimulus.

12. A method of estimating the intracranial pressure of the subject comprising the steps of:
(a) providing at least one sensory stimulus to the subject;
(b) sensing an analog electrical brain response of the subject to said at least one stimulus by means of an electrode;
(c) converting said analog response to a digital signal;
(d) determining a peak location in said digital signal by means for digital computing;
(e) generating an output signal representative of said peak location to indicate estimated intracranial pressure; and
(f) wherein said output signal indicates a range of estimated intracranial pressure.

13. A method of estimating the intracranial pressure of a subject comprising the steps of:
(a) providing at least one sensory stimulus to the subject;
(b) sensing an analog electrical brain response of the subject to said at least one stimulus by means of an electrode;
(c) converting said analog response to a digital signal;
(d) determining a peak location in said digital signal by means for digital computing;
(e) generating an output signal representative of said peak location to indicate estimated intracranial pressure;
(f) wherein said analog response is sampled at a plurality of intervals such that a plurality of discrete digital values are generated which represent said analog response;
(g) wherein said discrete digital values are each stored in a unique memory location;
(h) wherein a plurality of stimuli are provided and said discrete digital values corresponding to each said interval are summed; and
(i) monitoring said discrete digital values for an out-of-range condition and providing one additional stimulus when an out-of-range condition is sensed.

14. A method of estimating the intracranial pressure of a subject comprising the steps of:
(a) providing at least one sensory stimulus to the subject;
(b) sensing an analog electrical brain response of the subject to said at least one stimulus by means of an electrode;
(c) converting said analog response to a digital signal;
(d) determining a peak location in said digital signal by means for digital computing;
(e) generating an output signal representative of said peak location to indicate estimated intracranial pressure; and
(f) eliminating abnormal fluctuations in said analog response by means of a curve smoothing routine.

15. A method of estimating the intracranial pressure of a subject comprising the steps of:
(a) providing at least one sensory stimulus to the subject;
(b) sensing an analog electrical brain response of the subject to said at least one stimulus by means of an electrode;
(c) converting said analog response to a digital signal;
(d) determining a peak location in said digital signal by means for digital computing;
(e) generating an output signal representative of said peak location to indicate estimated intracranial pressure; and
(f) wherein said step of determining a peak location determines a peak in the second negative-going wave of said analog response.

16. A method of estimating the intracranial pressure of a subject comprising the steps of:
(a) providing at least one sensory stimulus to the subject;
(b) sensing an analog electrical brain response of the subject to said at least one stimulus by means of an electrode;
(c) converting said analog response to a digital signal;
(d) determining a peak location in said digital signal by means for digital computing;
(e) generating an output signal representative of said peak location to indicate estimated intracranial pressure;
(f) wherein said analog response is sampled at a plurality of intervals such that a plurality of discrete digital values are generated which represent said analog response; and
(g) wherein said step determining a peak location comprises analyzing said discrete digital values for a change in slope from negative to positive.

17. A method of estimating the intracranial pressure of a subject comprising the steps of:
(a) providing at least one sensory stimulus to the subject;

(b) sensing an analog electrical brain response of the subject to said at least one stimulus by means of an electrode;

(c) converting said analog response to a digital signal;

(d) determining a peak location in said digital signal by means for digital computing;

(e) generating an output signal representative of said peak location to indicate estimated intracranial pressure; and (f) generating an error signal if no said peak location is determined in said step of determining a peak location.

18. A method of estimating the intracranial pressure of a subject comprising the steps of:

(a) providing at least one sensory stimulus to the subject;

(b) sensing an analog electrical brain response of the subject to said at least one stimulus by means of an electrode;

(c) converting said analog response to a digital signal;

(d) determining a peak location in said digital signal by means for digital computing;

(e) generating an output signal representative of said peak location to indicate estimated intracranial pressure; and (f) generating an error signal if more than one peak location is determined in said step of determining a peak location.

19. An apparatus for estimating intracranial pressure of a subject comprising:

(a) means for generating a potential evoked by a sensory stimulus;

(b) means for measuring the value of the latency of a peak of said potential; and (c) means for comparing the value of said latency with known latency/intracranial pressure correlations to determine an estimated intracranial pressure.

20. An apparatus for estimating intracranial pressure of a subject comprising:

(a) an electrode adapted to be attached to the head of the subject to measure voltage potentials;

(b) means for providing a sensory stimulus to the subject;

(c) means for measuring the interval between said stimulus and a peak voltage potential on said electrode; and (d) means for identifying an estimated range of intracranial pressure corresponding to said measured interval.

21. An apparatus for estimating intracranial pressure of the subject comprising:

(a) a source of light disposed to be viewed by the subject;

(b) an electrode adapted to be attached to the subject's head to detect the subject's electrical brain activity;

(c) means for causing said source of light to flash, thereby stimulating electrical brain activity of the subject;

(d) computer means for detecting a latency of a peak in said electrical brain activity with respect to said flash of said source of light; and (e) output means for indicating a range of intracranial pressure determined with respect to said detected peak latency.

22. The apparatus of claim 21 further comprising storage media means for recording signals indicative of said electrical brain activity stimulated by said source of light.

23. The apparatus according to claim 22 further comprising microprocessor means for controlling said means for causing said light to flash, said storage media, and said output device.

* * * * *

UNITED STATES PATENT AND TRADEMARK OFFICE
CERTIFICATE OF CORRECTION

PATENT NO. : 4,564,022

DATED : Jan. 14, 1986

INVENTOR(S) : Rosenfeld et al.

It is certified that error appears in the above-identified patent and that said Letters Patent is hereby corrected as shown below:

Title page:

Under REFERENCES CITED, Allen, A.R.: "Sensor" should be --Sensory--.

Column 7, line 60, "21 to 196" should be --2 to 196--.

Signed and Sealed this

Twenty-third Day of September 1986

[SEAL]

Attest:

DONALD J. QUIGG

Attesting Officer

Commissioner of Patents and Trademarks